United States Patent
Anan et al.

(10) Patent No.: US 9,752,997 B2
(45) Date of Patent: Sep. 5, 2017

(54) CHARGED-PARTICLE-BEAM ANALYSIS DEVICE AND ANALYSIS METHOD

(71) Applicant: HITACHI, LTD., Chiyoda-ku, Tokyo (JP)

(72) Inventors: Yoshihiro Anan, Tokyo (JP); Masanari Koguchi, Tokyo (JP)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 15/308,563

(22) PCT Filed: May 30, 2014

(86) PCT No.: PCT/JP2014/064454
§ 371 (c)(1),
(2) Date: Nov. 2, 2016

(87) PCT Pub. No.: WO2015/181961
PCT Pub. Date: Dec. 3, 2015

(65) Prior Publication Data
US 2017/0067838 A1 Mar. 9, 2017

(51) Int. Cl.
*G21K 5/00* (2006.01)
*H01J 37/26* (2006.01)
*G01N 23/225* (2006.01)

(52) U.S. Cl.
CPC ....... *G01N 23/2252* (2013.01); *G01N 23/225* (2013.01)

(58) Field of Classification Search
USPC ........ 250/306, 307, 309–311, 440.11, 341.1, 250/341.2, 370.06, 370.09, 390.07, 396 R, 250/397, 492.1, 492.21, 492.3, 526; 378/45, 46, 64, 83, 85, 88, 90, 98.9, 378/98.11, 98.12, 140, 210
See application file for complete search history.

(56) References Cited

U.S. PATENT DOCUMENTS

| 5,299,138 A | * | 3/1994 | Fiori | G01N 23/20091 |
| | | | | 250/390.07 |
| 7,579,591 B2 | * | 8/2009 | Takakura | G01N 23/2252 |
| | | | | 250/306 |

(Continued)

FOREIGN PATENT DOCUMENTS

| JP | 5-242848 A | 9/1993 |
| JP | 2004-294168 A | 10/2004 |

(Continued)

*Primary Examiner* — Bernard Souw
(74) *Attorney, Agent, or Firm* — Miles & Stockbridge P.C.

(57) ABSTRACT

To provide a charged particle beam analyzer enabling an efficient and high-sensitivity analysis of a microscopic light element contained in a heavy metal sample, the charged particle beam analyzer equipped with a WDX spectrometer includes a storage unit 126 having stored therein a correlation database between average atomic numbers and WDX background intensity values obtained with use of a plurality of standard samples and a WDX background processing means 146 including a means 147 for calculating an average atomic number for a sample 129 and a means for eliminating a WDX background intensity value derived from the average atomic number for the sample 129 and the correlation database from a WDX spectrum for the sample 129.

15 Claims, 13 Drawing Sheets

(56) References Cited

U.S. PATENT DOCUMENTS

| | | | | |
|---|---|---|---|---|
| 8,481,932 B2* | 7/2013 | Anan | ............... | H01J 37/228 |
| | | | | 250/306 |
| 9,601,308 B2* | 3/2017 | Anan | ............. | G01N 23/2252 |
| 2008/0111072 A1* | 5/2008 | Takakura | .......... | G01N 23/2252 |
| | | | | 250/310 |
| 2012/0257720 A1* | 10/2012 | Anan | ............... | H01J 37/228 |
| | | | | 378/64 |
| 2015/0318144 A1* | 11/2015 | Anan | ............. | G01N 23/2252 |
| | | | | 250/306 |

FOREIGN PATENT DOCUMENTS

| | | |
|---|---|---|
| JP | 2008-122267 A | 5/2008 |
| JP | 2009-002658 A | 1/2009 |
| JP | 2009-264926 A | 11/2009 |
| JP | 2012-220337 A | 11/2012 |

\* cited by examiner

ROWLAND CIRCLE

MAP IMAGE (ENERGY E1)

BACKGROUND IMAGE (ENERGY E2)

CHARGED-PARTICLE-BEAM ANALYSIS DEVICE AND ANALYSIS METHOD

TECHNICAL FIELD

The present invention relates to a charged particle beam analyzer and an analysis method.

BACKGROUND ART

Known as an X-ray analysis technology in a nanometer-scale region is a S(T)EM-EDX or a S(T)EM-WDX for scanning a sample with use of an ultra-micro electron probe and dispersing an X-ray generated from a local region irradiated with an electron beam (SEM: Scanning Electron Microscope, STEM: Scanning Transmission Electron Microscope, EDX: Energy Dispersive X-ray Spectroscopy, and WDX: Wavelength Dispersive X-ray Spectroscopy). The S(T)EM-EDX or the S(T)EM-WDX is an apparatus in which the S(T)EM is equipped with an energy dispersive X-ray spectrometer (EDX) or a wavelength dispersive X-ray spectrometer (WDX).

In the EDX spectrometer, a lithium drifted silicon semiconductor detector or, in recent years, a silicon drift detector (SDD) is used as a detector, and by dispersing a pulse signal generated by the semiconductor detector with use of a multi-channel pulse-height analyzer, parallel detection is enabled. In the WDX spectrometer, a diffraction grating for monochromating the X-ray and a detector for detecting the monochromated X-ray are used, and serial detection is performed in which the diffraction grating and the detector are operated. The WDX spectrometer has an energy resolution of several eV to several tens of eV, which is one or more digits higher than that of the EDX spectrometer, which is 120 eV.

The WDX spectrometer is a detector in which a diffraction grating serving as a diffraction grating is operated based on Bragg diffraction shown in Equation (1). In the equation, d is crystal lattice plane spacing of the diffraction grating, $\theta$ is an incident angle of the X-ray in the grating surface, n is a diffraction order, and $\lambda$ is a wavelength of the X-ray.

$$2d \sin \theta = n\lambda \quad (1)$$

The WDX spectrometer is generally categorized into two types. One is a type of dispersing and detecting an X-ray while rotating a multilayered flat-shaped diffraction grating 113a and operating a WDX X-ray detector 114 as illustrated in FIG. 2. The WDX spectrometer of this type turns an X-ray entering the flat-shaped diffraction grating 113a into a parallel X-ray 134a. Also, to improve a yield of an X-ray 134 generated from a sample 129 by irradiation with a primary electron beam 128, an X-ray condensing lens 112 is installed between the sample 129 and the flat-shaped diffraction grating 113a (e.g., PTL 1). To turn the X-ray 134 entering the flat-shaped diffraction grating 113a into the parallel X-ray 134a, a slit is installed between the sample 129 and the flat-shaped diffraction grating 113a in some cases. The other is, as illustrated in FIG. 3, a type of including a curved diffraction grating 113b called Johann or Johansson geometry and the WDX X-ray detector 114 and dispersing and detecting an X-ray while operating the curved diffraction grating 113b and the WDX X-ray detector 114 on a Rowland circle.

The WDX spectrometer in principle detects higher order X-ray in which n shown in Equation (1) are two or more as well. Since the spectrum of the higher order X-rays may overlap with a spectrum that is desired to be measured, which may cause a false detection. To prevent the false detection caused by the higher order X-rays, pulse-height distribution data shapes are distinguished from each other with use of an energy difference between the X-rays entering the WDX X-ray detector 114 (e.g., PTL 2).

As for detection of a light element in the above EDX and WDX spectrometers, in recent years, the EDX spectrometer dispenses with a detection window to prevent the window material from absorbing an X-ray of the light element, and the detection sensitivity of the light element is improved. However, since the EDX spectrometer has as a low energy resolution as 120 eV, in detection of a B (boron) element, for example, a tail part of a Carbon(C) X-ray peak as a C contamination generated by irradiation with an electron beam overlaps with a Boron X-ray peak, and the minimum detection sensitivity is thus about 10%.

In detection of a light element in the WDX spectrometer, a window material of the spectrometer is thinned to restrict absorption of an X-ray of the light element into the window material. In addition, by using an X-ray condensing lens formed in a shape contributing to an increase of the collection rate of the X-ray of the light element, the detection sensitivity of the light element is improved (PTL 3). Since the energy resolution of the WDX spectrometer is one digit higher than that of the EDX spectrometer, the overlap of the tail of the C peak with the B peak, which has been a problem in the aforementioned EDX spectrometer, is drastically decreased, and the WDX spectrometer can detect B of less than 1% except detection of a light element in a heavy element.

CITATION LIST

Patent Literature

PTL 1: JP 2004-294168 A
PTL 2: JP 2009-264926 A
PTL 3: JP 2012-220337 A

SUMMARY OF INVENTION

Technical Problem

An X-ray analysis of a light element contained in a heavy metal material such as a steel material and a permanent magnet, which is expected to be increasingly demanded in the future, has been considered further. As described above, by using the WDX spectrometer, a light element contained in a sample other than a heavy metal material can be detected at a minimum detection sensitivity of 1% or less. This time, an analysis technique enabling high-sensitivity detection of a light element in a heavy metal material is considered further.

As described above, the WDX spectrometer detects intensity of an X-ray while operating the diffraction grating and the detector. In the graph illustrated in FIG. 4, the horizontal axis represents a rotation angle of the diffraction grating while the vertical axis represents X-ray intensity. The graph illustrates a WDX spectrum obtained by the WDX spectrometer. Since the rotation angle in the horizontal axis corresponds to energy based on Equation (1), a value in the horizontal axis can be converted into energy.

When a sample is irradiated with an electron beam, braking radiation is generated, and the braking radiation becomes a background of an X-ray spectrum. In a case in which a sample having a low atomic number containing a light element is irradiated with an electron beam, and in which an X-ray spectrum generated from the sample is obtained, background intensity generated from the sample is low, and a spectrum in which the ratio of a peak (P) to a background (B) (P/B ratio) is high is obtained as an X-ray spectrum 4-1 in FIG. 4. On the other hand, in a case of a heavy element, since the braking radiation is generated much, the background of the X-ray spectrum is high. Also, when a sample transmits an X-ray, the X-ray is absorbed into the sample itself. An absorption coefficient representing a rate of the X-ray absorbed into the sample is proportional to the fourth power of an atomic number Z constituting a substance. Thus, in a case of a heavy element sample, a light element X-ray generated from the sample is absorbed into the sample more. As a result, the X-ray spectrum of the light element contained in the heavy metal is an X-ray spectrum 4-2 illustrated in FIG. 4, in which the background is high, and in which peak intensity of the light element is low (the P/B ratio is low). Accordingly, the detection sensitivity of the light element in the heavy metal is significantly lowered.

FIG. 5 is a schematic view of an evaluated sample. The sample contains two regions consisting of a location A and a location B. The location A is a heavy element A having an atomic number $Z_A$, and the location B is a heavy element B having an atomic number $Z_B$. The location A contains a small amount of light element (LE). The atomic number $Z_B$ is higher than $Z_A$. The X-ray spectra in a low energy region obtained in the location A and the location B are a spectrum A and a spectrum B illustrated in FIG. 6, respectively. The spectrum A is a spectrum in which an X-ray peak C of a signal $S_{LE}$ resulting from the light element is superposed on background intensity $BG_A$ caused mainly by the braking radiation resulting from the heavy element A. The spectrum B expresses only the background as the braking radiation resulting from the heavy element B with no peak since the location B contains no light element. When an element map image is to be measured by the WDX spectrometer, the diffraction grating is set and fixed at a position at which the intensity of the X-ray spectrum to be measured is the highest, that is, at an angle satisfying the Bragg conditions in Equation (1), and the X-ray intensity to be obtained under the conditions of the detection system in which the diffraction grating is fixed is detected in synchronization with an electron beam scanning signal to be emitted to the sample. That is, when map measurement for the sample illustrated in FIG. 5 is to be conducted, the conditions of the detection system in which the diffraction grating is fixed at an energy position E1 illustrated in FIG. 6 are set, and the X-ray intensity at the energy position E1 is detected in synchronization with the electron beam scanning signal.

FIG. 7 illustrates a light element map image of the sample illustrated in FIG. 5. The location A contains a light element while the location B contains no light element. In the map image in FIG. 7, the X-ray map intensity is higher in the location B than in the location A, which shows a result in which the location B, rather than the location A, contains a light element. As for the X-ray intensity at the energy position E1 illustrated in FIG. 6, background intensity $BG_B$ at the location B is higher than spectrum intensity $S_A$ at the location A. Thus, the X-ray image intensity in the location A in FIG. 7 is lower than that in the location B. The reason for this is that, although the location B contains no light element while the location A contains a light element, the background intensity $BG_B$ caused by the braking radiation of the heavy element B is higher than the intensity $S_A$, which is the sum of the light element peak SL and the background intensity $BG_A$ resulting from the heavy element A. Accordingly, as described above, in a sample containing heavy elements having different atomic numbers Z, braking radiation background intensity varies significantly, which may cause false detection in a light element map image.

To reduce the aforementioned false detection caused by a difference in braking radiation background intensity due to a difference in atomic number between heavy elements, a method for using a difference image between two map images is raised. One out of the two map images is the light element map image illustrated in FIG. 7 obtained at the energy position E1 in FIG. 6, and the other is a background map image (FIG. 8) obtained at an energy position E2 illustrated in FIG. 6, which is a tail of the light element peak. By subtracting the background map image in FIG. 8 from the map image in FIG. 7, a map image illustrated in FIG. 9 only for the peak intensity $S_{LE}$ resulting from the light element, in which, in terms of the spectrum A, the peak intensity $S_{LE}$ resulting from the light element is extracted, and in which, in terms of the spectrum B, the braking radiation background of the heavy element B is eliminated, can be obtained.

However, in the above method, since two map images need to be obtained, it takes twice as long for the measurement. Also, as a fundamental problem, it is found that obtaining the map image only for the peak intensity SL as illustrated in FIG. 9 is actually difficult especially in a case of a light element.

Irradiating a sample with an electron beam causes a surface of the sample to be contaminated, a light element X-ray generated from the sample is absorbed into the contaminated part, and the amount of the X-ray to be detected by an X-ray detector is decreased. Also, the contamination causes changes in background intensity, and the spectrum shape is changed to a spectrum shape in which the background increases and in which the peak is small as in a spectrum A1 and a spectrum B1 illustrated in FIG. 10. Especially, the background image, which is to be obtained for the second time, is largely influenced by many contaminated parts formed on the surface of the sample. This causes a problem in which an image obtained by subtracting a map image at the energy position E2 from a map image at the energy position E1 is not like the map image illustrated in FIG. 9 only for the peak intensity $S_{LE}$ resulting from the light element.

An object of the present invention is to provide a charged particle beam analyzer and an analysis method enabling an efficient and high-sensitivity analysis of a microscopic light element contained in a heavy metal sample such as a steel material and a permanent magnet.

The above object and other objects, and novel characteristics of the present invention will be made clear by description of the present specification and the attached drawings.

Solution to Problem

An embodiment to solve the above issue is a charged particle beam analyzer including a charged particle beam optical system, a sample stage for mounting a sample thereon, an X-ray spectrometer, a control unit, and an operation unit, and controlling the charged particle beam optical system by means of the control unit to irradiate the sample with a charged particle beam, detecting an X-ray generated from the sample by means of the X-ray spectrometer, and analyzing the sample with use of detected information by means of the operation unit, wherein the X-ray spectrometer is a wavelength dispersive X-ray spectrometer (WDX spectrometer), and the operation unit includes:
a storage unit having stored therein a correlation database between a plurality of average atomic numbers and WDX background intensity values obtained with use of a plurality of standard samples; and
a WDX background processing means including an average atomic number calculation means for calculating an average atomic number for the sample and a background elimination means for eliminating a WDX background intensity value derived from the average atomic number for the sample calculated by the average atomic number calculation means and the correlation database stored in the storage unit from a WDX spectrum for the sample obtained with use of the X-ray spectrometer.

In addition, there is provided a charged particle beam analyzer including a charged particle beam optical system, a sample stage for mounting a sample thereon, an X-ray spectrometer, a control unit, and an operation unit, and controlling the charged particle beam optical system by means of the control unit to irradiate the sample with a charged particle beam, detecting an X-ray generated from the sample by means of the X-ray spectrometer, and performing map evaluation for the sample with use of detected information, wherein the X-ray spectrometer is a wavelength dispersive X-ray spectrometer (WDX spectrometer), and
the operation unit includes:
a storage unit having stored therein a correlation database between a plurality of average atomic numbers and WDX background intensity values obtained with use of a plurality of standard samples;
a WDX background processing means including an average atomic number calculation means for calculating an average atomic number map with use of X-ray energy corresponding to a specific light element on a surface of the sample and a background elimination means for eliminating a WDX background intensity map derived from the average atomic number map for the surface of the sample calculated by the average atomic number calculation means and the correlation database stored in the storage unit from a WDX spectrum map for the sample obtained with use of the X-ray spectrometer; and
an image display unit for displaying the WDX background intensity map derived from the correlation database stored in the storage unit.

In addition, there is provided an analysis method including:
a first step of creating a correlation database between a plurality of average atomic numbers and WDX background intensity values with use of a plurality of standard samples and storing the correlation database in a storage unit; and
a second step of calculating an average atomic number for an evaluated sample and eliminating a WDX background intensity value derived from the calculated average atomic number for the evaluated sample and the correlation database stored in the storage unit from a WDX spectrum for the sample obtained with use of a wavelength dispersive X-ray spectrometer.

Advantageous Effects of Invention

Through brief description of an effect achieved by representative components of the invention disclosed herein, it is possible to provide a charged particle beam analyzer and an analysis method enabling an efficient and high-sensitivity analysis of a microscopic light element contained in a heavy metal sample.

DESCRIPTION OF EMBODIMENTS

Figure 1:
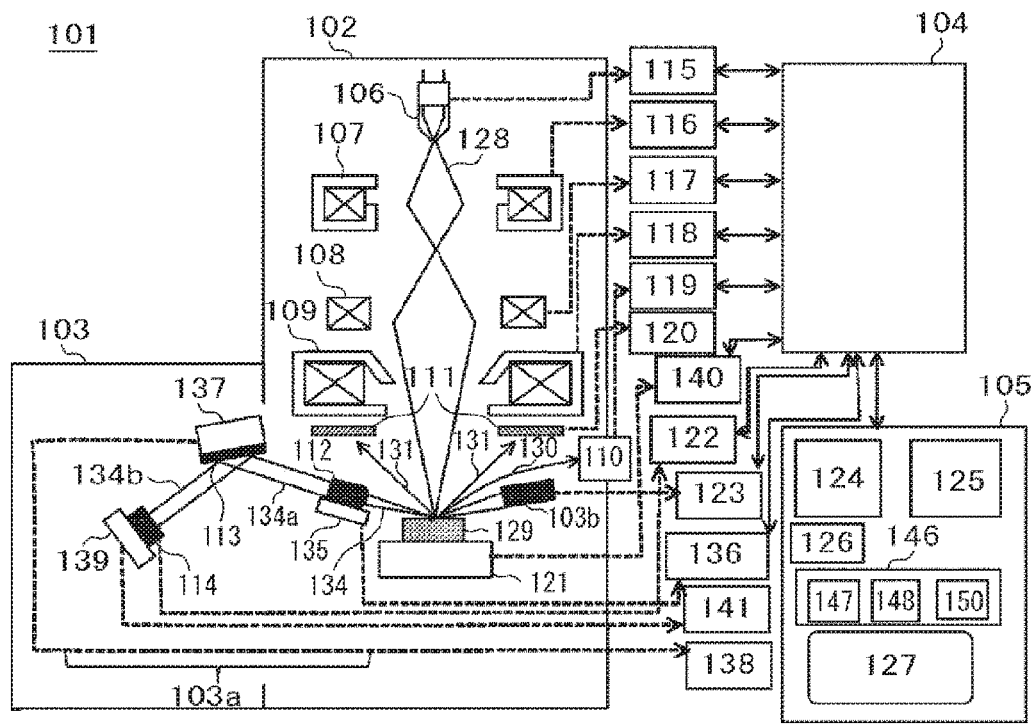
FIG. 1 is a schematic overall configuration diagram (partially a cross-sectional view) for illustrating a configuration of an electron beam analyzer according to Embodiment 1 of the present invention.
Figure 2:
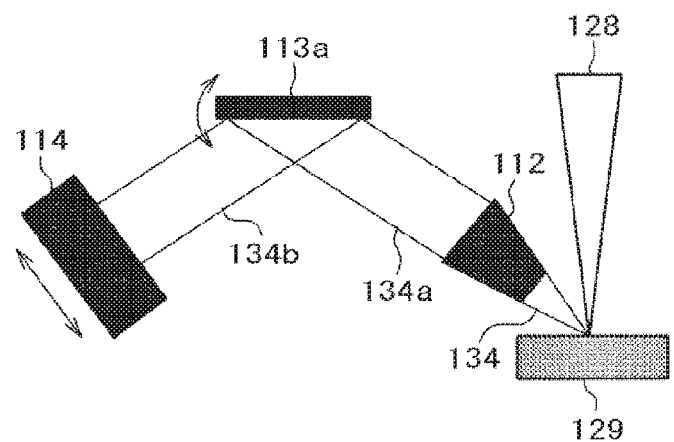
FIG. 2 is a schematic side view of a conventional wavelength dispersive X-ray spectrometer (WDX) using a multilayered flat-shaped diffraction grating.
Figure 3:
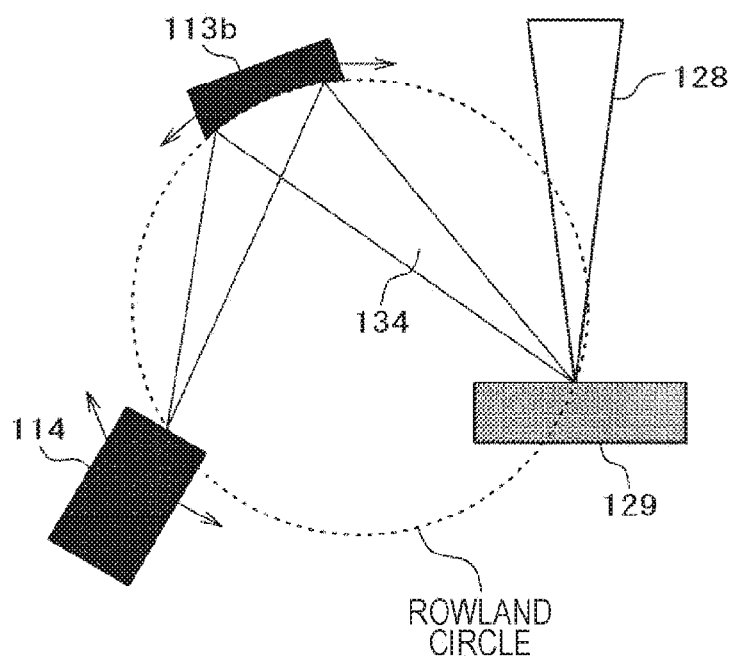
FIG. 3 is a schematic side view of a conventional wavelength dispersive X-ray spectrometer (WDX) using a curved diffraction grating.
Figure 4:
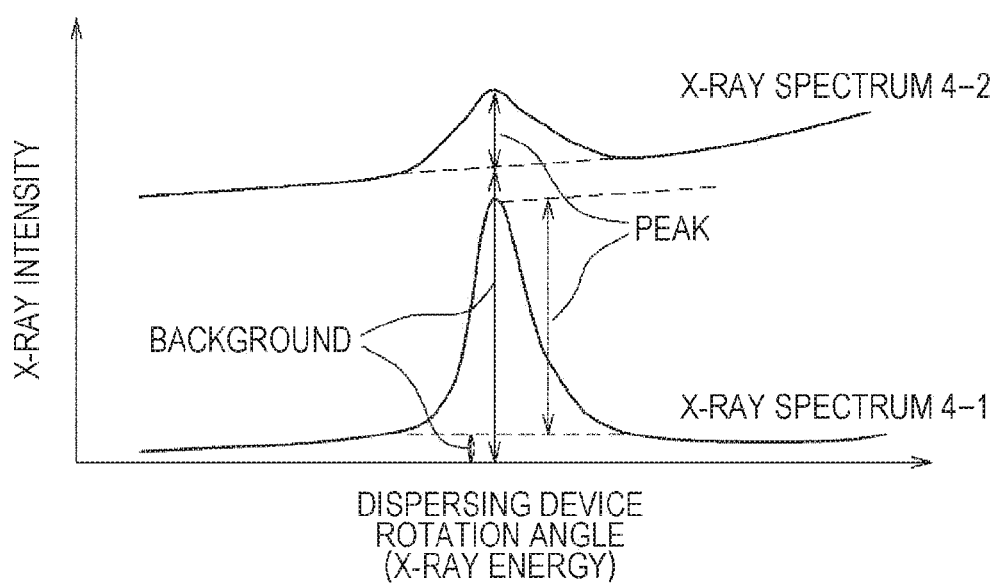
FIG. 4 illustrates examples of light element WDX spectra for describing a problem.
Figure 5:
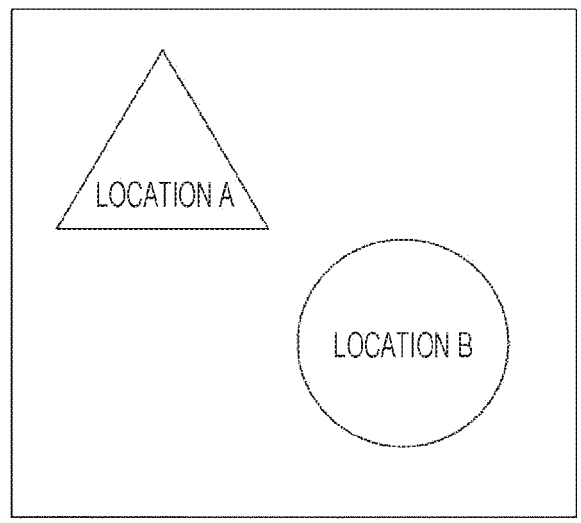
FIG. 5 is a schematic plan view illustrating an example of an evaluated sample for describing the problem.
Figure 6:
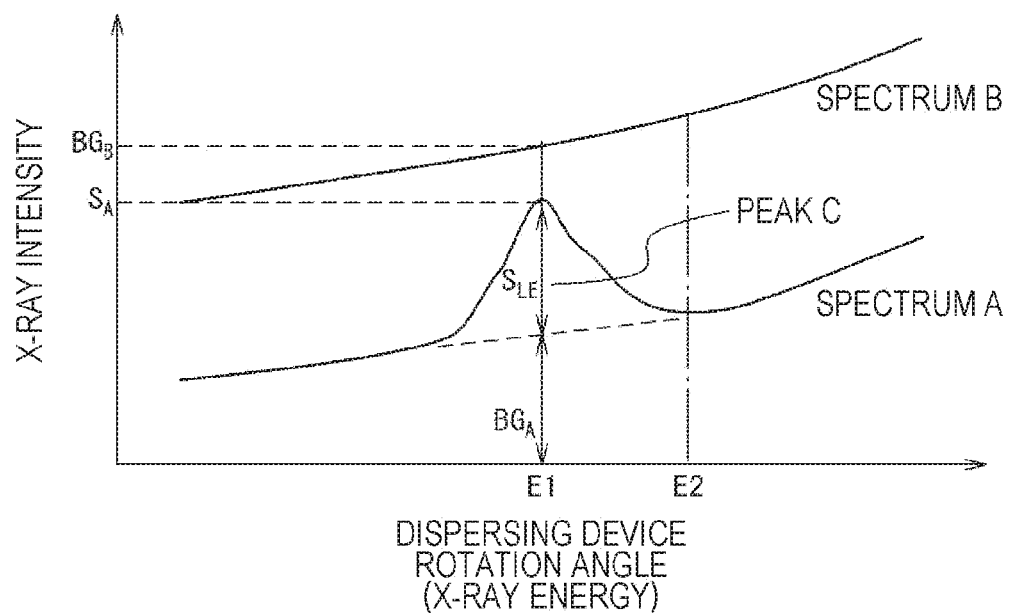
FIG. 6 illustrates examples of light element WDX spectra for describing the problem.
Figure 7:
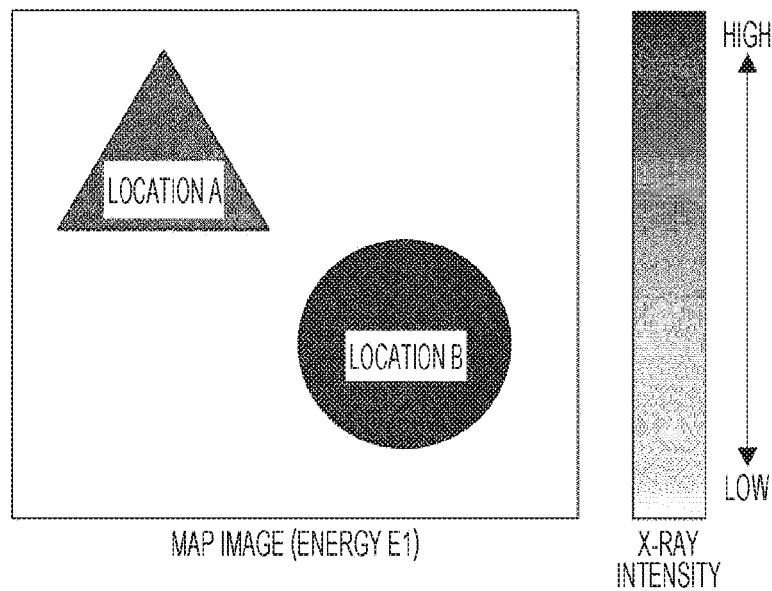
FIG. 7 is a plan view illustrating an example of a light element WDX map image for describing the problem.
Figure 8:
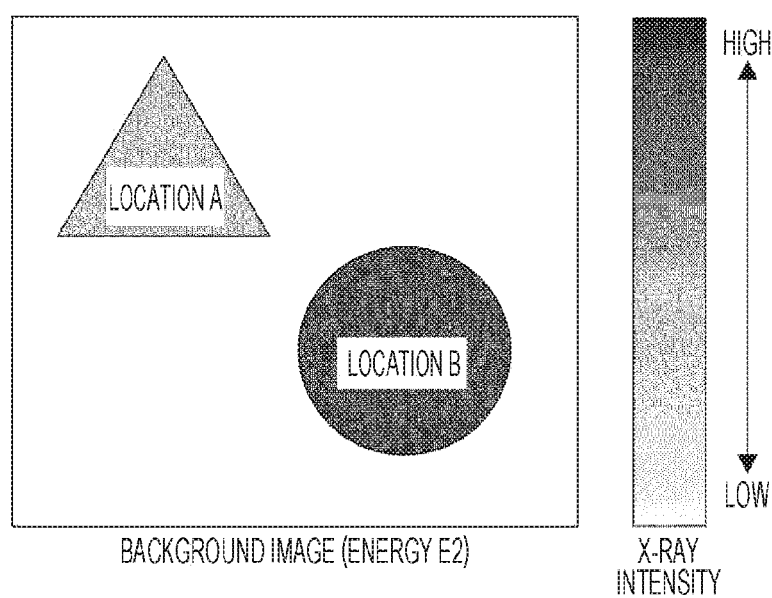
FIG. 8 is a plan view illustrating an example of a light element WDX background image for describing the problem.
Figure 9:
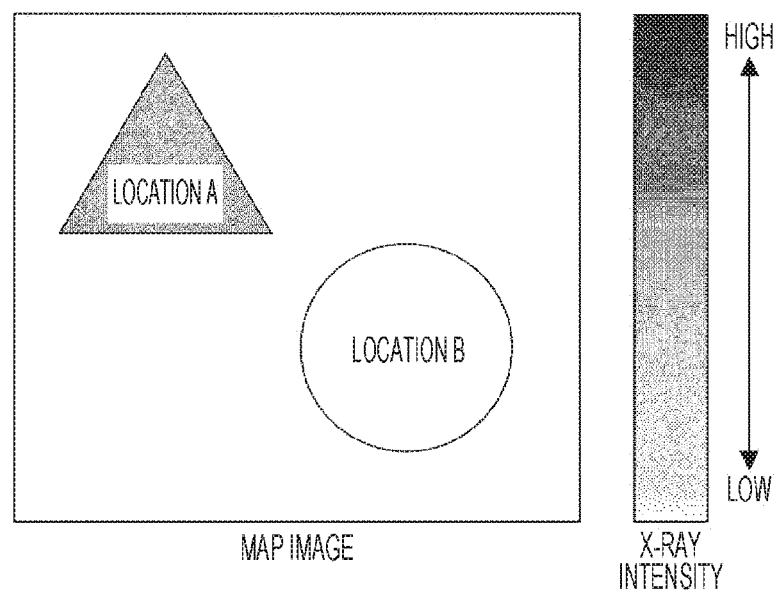
FIG. 9 is a plan view illustrating an example of a light element WDX map image for describing the problem.
Figure 10:
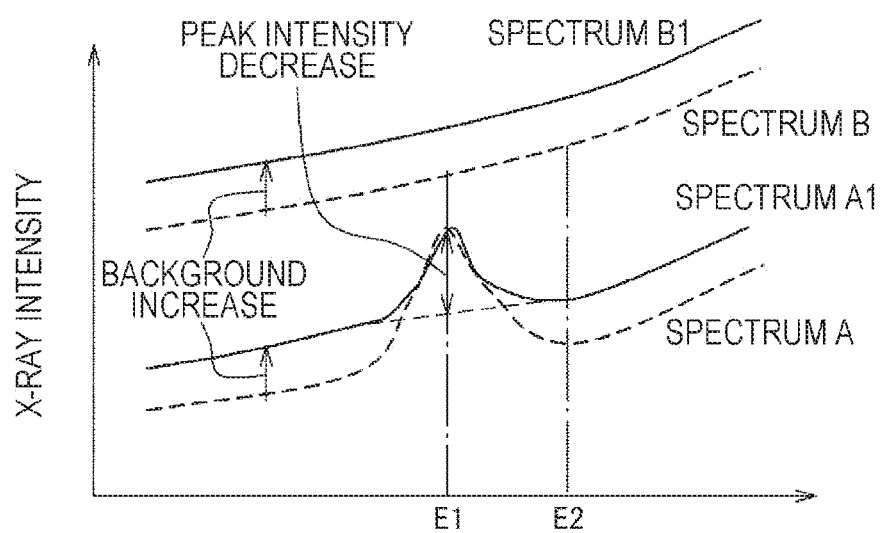
FIG. 10 illustrates examples of light element WDX spectra for describing the problem.

A charged particle beam analyzer according to the present invention, such as an electron beam analyzer, includes an electron microscope device, a wavelength dispersive X-ray spectrometer (WDX spectrometer), an energy dispersive X-ray spectrometer (EDX spectrometer), and the like. The electron microscope includes an electron optical system for irradiating a sample with an electron beam and a means for detecting a secondary electron or a backscattered electron generated from a part irradiated with the electron beam or detecting an electron transmitted in the sample or a scattered electron. The WDX spectrometer includes an X-ray condensing lens for condensing an X-ray generated from the part irradiated with the electron beam, a diffraction grating for dispersing the X-ray condensed by the X-ray lens, and an X-ray detector for detecting the X-ray dispersed by the diffraction grating. The EDX spectrometer includes a means for converting the X-ray generated from the part irradiated with the electron beam into a pulse signal and a means for separating and detecting the pulse signal by means of a multi-channel pulse-height analyzer. The charged particle beam analyzer configured as above further includes an average atomic number calculation means for measuring an average atomic number Z in a sample from X-ray intensity detected by the EDX spectrometer, the EDX spectrometer detecting the X-ray generated by irradiating the sample with electron beam, a means for detecting, by means of the WDX spectrometer, X-ray intensity in a low energy region in the X-ray generated from the sample at the same time as the EDX X-ray detection, and a means for processing a background from a spectrum obtained by the WDX spectrometer based on correlation data between average atomic numbers obtained by the average atomic number calculation means and background signals in the low energy region detected by the WDX spectrometer.

That is, by using the correlation data between the average atomic numbers obtained by the average atomic number calculation means and the background signals in the low energy region detected by the WDX spectrometer, conventional false detection in light element detection caused by a background difference due to a difference in atomic number between heavy elements is prevented. Also, obtainment of a background map image performed by the WDX, which is conventionally required for braking radiation background processing, is dispensed with, to eliminate a waste of time and enable a light element analysis in a short time. Further, since changes of a background shape due to irradiation with the electron beam can be reduced much further than in a conventional case, a high-sensitivity analysis can be achieved.

In the following embodiments, an electron beam analyzer in which a scanning electron microscope (SEM) using an electron beam is equipped with an X-ray analyzer such as an EDX and a WDX will be described in particular. However, a scanning transmission electron microscope (STEM) or a secondary ion mass spectrometer can be equipped with the X-ray analyzer. Also, a backscattered electron detector can be used instead of the EDX spectrometer.

Hereinbelow, embodiments of the present invention will be described in detail based on the drawings. It is to be noted that similar components are basically shown with the same reference signs, and description of the duplicate components is omitted.

Embodiment 1

FIG. 1 is a schematic view illustrating a configuration example of an electron beam analyzer 101 according to Embodiment 1. The electron beam analyzer 101 illustrated in FIG. 1 includes a scanning electron microscope device 102, an X-ray analysis device 103, a control system 104, and an operation unit 105. The scanning electron microscope device 102 includes an electron gun 106, a condenser lens 107, an electron beam deflector 108, an objective lens 109, a sample stage 121, a secondary electron detector 110, and a backscattered electron detector 111. The X-ray analysis device 103 includes a WDX spectrometer 103a and an EDX spectrometer 103b. The WDX spectrometer 103a includes an X-ray condensing lens 112, a diffraction grating 113, and a WDX X-ray detector 114. The control system 104 includes an electron gun control unit 115, a condenser lens control unit 116, an electron beam deflector control unit 117, an objective lens control unit 118, a secondary electron detection system circuit control unit 119, and a backscattered electron detection system circuit control unit 120, a stage control unit 140, a WDX X-ray detection system circuit control unit 122, an EDX X-ray detection system circuit control unit 123, an X-ray condensing lens driving control unit 136, a diffraction grating driving control unit 138, and a WDX X-ray detector driving control unit 141. The operation unit 105 includes an image display unit 124, an X-ray spectrum display unit 125, a storage unit 126 configured to store a stage position, a secondary electron or backscattered electron image, an X-ray image, a spectrum, and the like, a WDX background processing means 146, and an operating screen 127.

Figure 11:
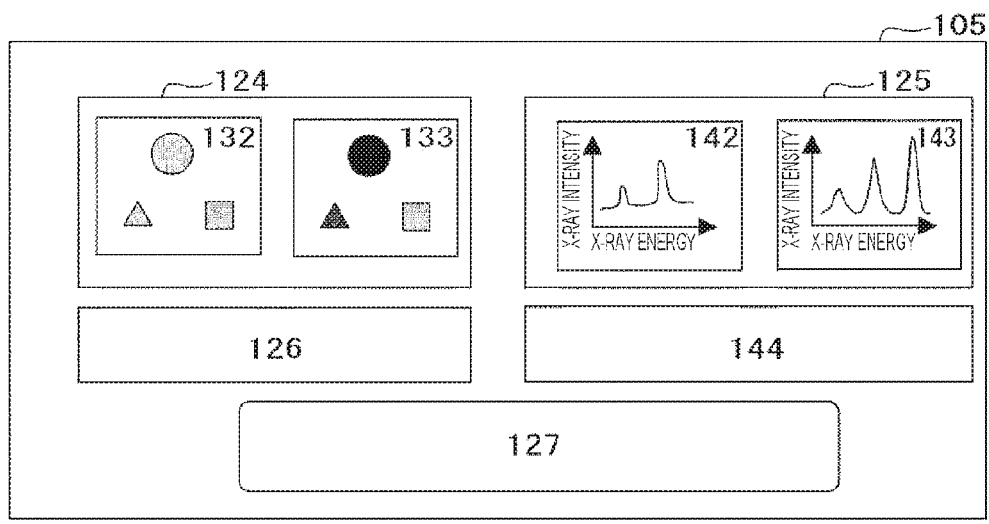
FIG. 11 is a schematic view illustrating an operation unit in the electron beam analyzer according to Embodiment 1 of the present invention.

A primary electron beam 128 generated from the electron gun 106 is narrowed down in the objective lens 109 and is emitted to a sample 129. When the primary electron beam 128 is emitted to the sample 129, the scanning speed and the scanning region are changed by the deflector 108. In accordance with the scanning speed, a secondary electron 130 or a backscattered electron 131 generated from a part irradiated with the primary electron beam 128 is detected in the secondary electron detector 110 or the backscattered electron detector 111. By outputting the secondary electron or backscattered electron signal detected in the secondary electron detector 110 or the backscattered electron detector 111 in synchronization with a scanning signal of the primary electron beam 128, a secondary electron image 132 and a backscattered electron image 133 of the sample 129 are displayed on the image display unit 124 as illustrated in FIG. 11.

In the WDX spectrometer 103a included in the electron beam analyzer 101, an X-ray 134 generated from the part of the sample 129 irradiated with the primary electron beam 128 is condensed and parallelized in the X-ray condensing lens 112, a parallel X-ray 134a enters the diffraction grating 113 for dispersion, and an X-ray 134b dispersed by the diffraction grating 113 is detected in the WDX X-ray detector 114. The X-ray condensing lens 112 can be moved to and be installed in a position in which the collection rate of the X-ray 134 is high by an X-ray lens driving unit 135. The angle of the diffraction grating 113 is adjusted in a diffraction grating driving unit 137, and the position of the WDX X-ray detector 114 is adjusted in a WDX detector driving unit 139. Also, although only one diffraction grating 113 is illustrated for convenience, two or more diffraction gratings of different types are actually provided so that any of the diffraction gratings may be selected and installed by the diffraction grating driving unit 137 in accordance with the energy of the X-ray to be detected. The EDX spectrometer 103b is configured to detect the X-ray 134 generated from the part of the sample 129 irradiated with the primary electron beam 128, and the EDX X-ray detection system circuit control unit 123 is configured to disperse the detected X-ray 134 per energy. A WDX spectrum 142 and an EDX spectrum 143 obtained by dispersing the X-ray 134 in the WDX spectrometer 103a and the EDX spectrometer 103b are displayed on the spectrum display unit 125 illustrated in FIG. 11.

Figure 12:
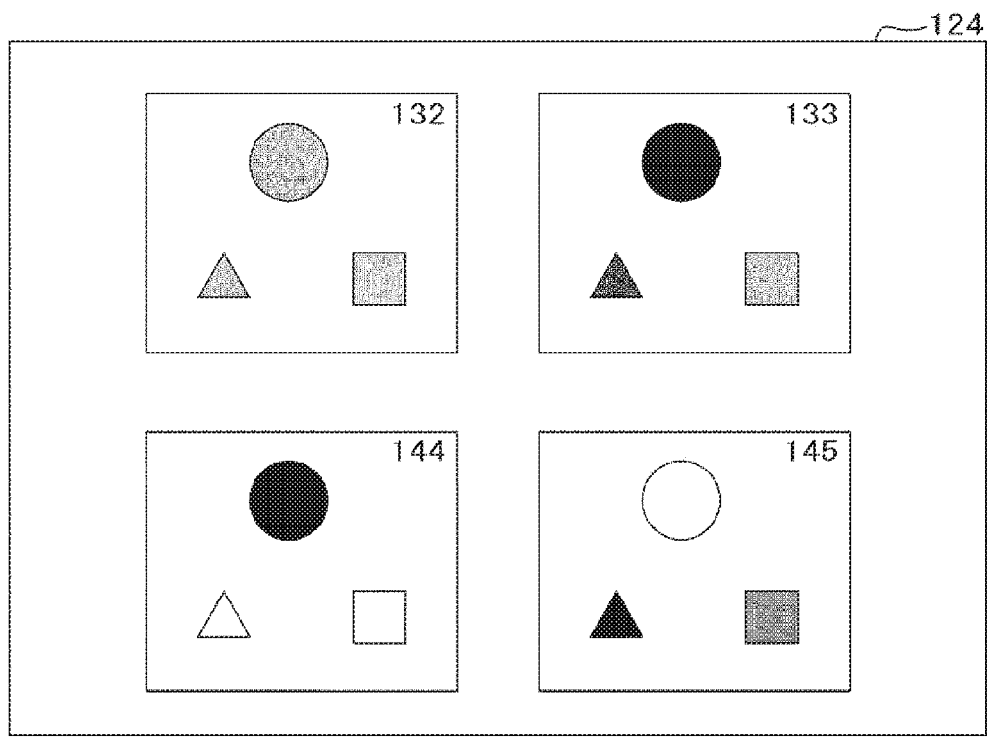
FIG. 12 is a schematic view illustrating an image display unit in the electron beam analyzer according to Embodiment 1 of the present invention.

In a similar manner to that in the case of the secondary electron image 132, by selecting X-ray intensity of a part of the WDX spectrum 142 obtained by dispersing the X-ray in the WDX spectrometer 103a and outputting an X-ray signal in synchronization with a scanning signal of the primary electron beam 128, a WDX element map image 144 can be displayed on the image display unit 124. In the case of using the EDX spectrometer 103b, an EDX element map image 145 can be displayed on the image display unit 124 in a similar manner to the above. By switching the image output of the image display unit 124, any of desired images can be displayed from among the secondary electron image 132, the backscattered electron image 133, the WDX element map image 144, and the EDX element map image 145. Also, as illustrated in FIG. 12, four screens can be provided in the image display unit 124 so that the secondary electron image 132, the backscattered electron image 133, the WDX element map image 144, and the EDX element map image 145 can be displayed simultaneously.

The electron beam analyzer 101 configured as above is characterized by further including the WDX background processing means 146 for processing a WDX background in a low energy region to be detected by the WDX spectrometer 103a. The WDX background processing means 146 includes the following means.
(1) An average atomic number calculation means 147 for measuring an average atomic number contained in a sample from the EDX spectrum 143 detected by the EDX spectrometer 103b. The calculated average atomic number can be displayed on any of the display units.
(2) A WDX background measurement means 148 for detecting in the WDX spectrometer 103a WDX background intensity in the low energy region obtained in the WDX spectrometer 103a at the same time as the X-ray detection in the EDX spectrometer 103b.
(3) A correlation data calculation means 150 for calculating correlation data 149 between average atomic numbers and WDX background intensity values 51 from a measurement result of the plurality of average atomic numbers and WDX background intensity values obtained by the above means (1) and (2) with use of a plurality of standard samples 129a.
(4) A WDX background intensity calculation means for obtaining a light element spectrum 142 for an evaluated sample 129b by means of the WDX spectrometer 103a, simultaneously measuring an X-ray spectrum 143 for the evaluated sample 129b by means of the EDX spectrometer 103b, and calculating a WDX background intensity value for the evaluated sample based on an average atomic number for the evaluated sample calculated from the EDX spectrum 143 by the average atomic number calculation means 147 and the correlation data 149 obtained by the above means (3). This means can be included in the WDX background processing means 146.
(5) A background elimination means for eliminating the WDX background intensity value 51 calculated by the above means (4) from the WDX spectrum 142 for the evaluated sample. This means can be included in the WDX background processing means 146.

Figure 13:
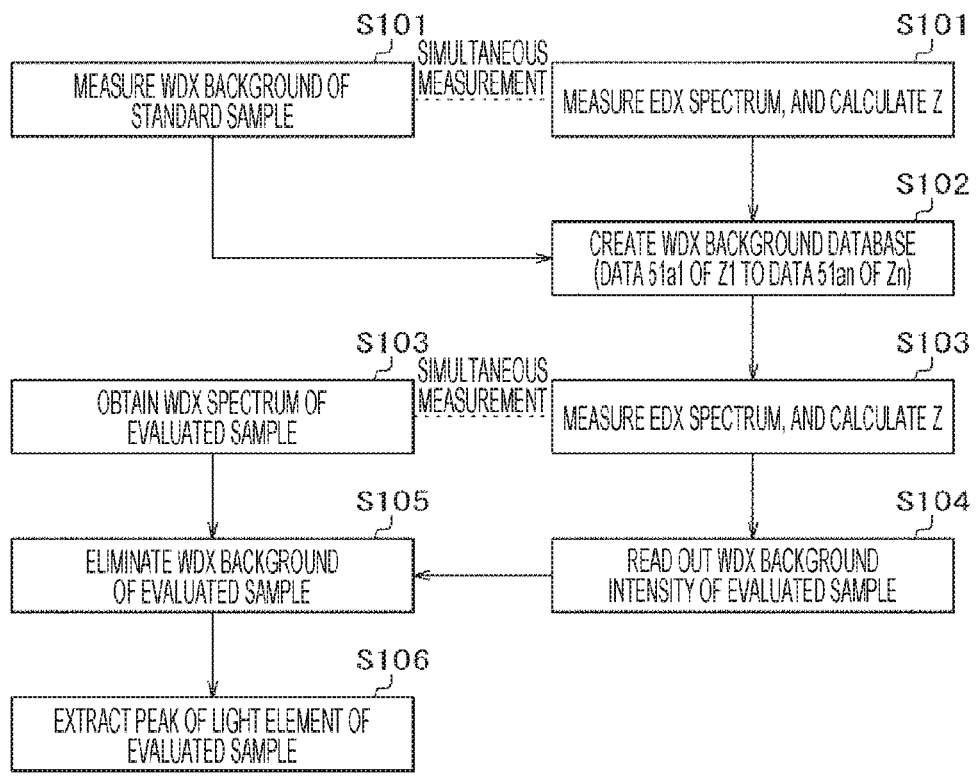
FIG. 13 is a flowchart illustrating an example of background processing in an analysis method according to Embodiment 1 of the present invention.
Figure 15:
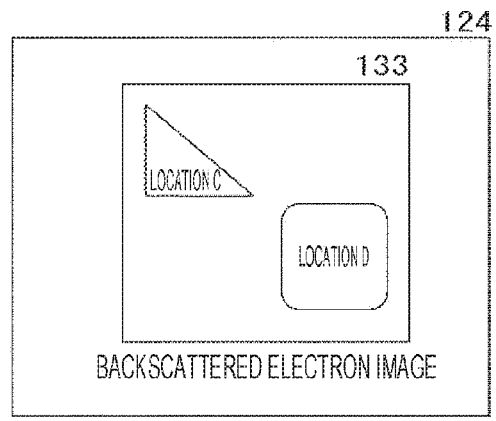
FIG. 15 is a display image illustrating an example of a backscattered electron image for a sample used for evaluation in the electron beam analyzer according to Embodiment 1 or 2 of the present invention.

Next, an example in which the electron beam analyzer 101 has been applied to detection of a light element in a heavy metal will be described. FIG. 13 is an example of a flow illustrating the present method. A backscattered electron image of an evaluated sample is illustrated in FIG. 15, and heavy element (a heavy element C and a heavy element D) regions in a location C and a location D are evaluated. The region in the location C contains a light element, and the average atomic numbers of the location C and the location D are $Z_C$ and $Z_D$. The atomic number $Z_C$ is higher than the atomic number $Z_D$.

First, a WDX spectrum 142a1 and an EDX spectrum 143a1 for a standard sample 129a1 are simultaneously obtained by the WDX spectrometer 103a and the EDX spectrometer 103b. The energy range of the WDX spectrum 142a is a low energy region for detecting a light element, the same shall apply hereinbelow, and the phrase "low energy region" is thus omitted. Based on the obtained EDX spectrum 143a1, an average atomic number Za1 is calculated by the average atomic number calculation means 147 (step S101).

Figure 14:
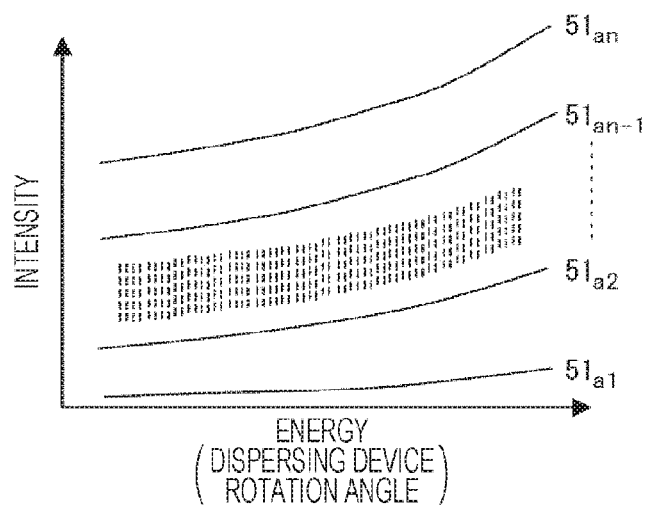
FIG. 14 illustrates WDX background data per average atomic number to be created in an electron beam analyzer according to Embodiment 1 or 2 of the present invention.

The measured WDX spectrum 142a1 is a background 51al having the average atomic number Za1 as illustrated in FIG. 14. The series of operations in the step S101 are performed with use of a plurality of standard samples 129a1 to 129an to obtain background data 51al to background data 51an of WDX spectra having average atomic numbers Z1 to Zn illustrated in FIG. 14 (step S102).

Subsequently, a WDX spectrum 142 and an EDX spectrum 143 for the location C in an evaluated sample 129b containing a light element sample in a heavy element are obtained by the WDX spectrometer 103a and the EDX spectrometer 103b, respectively. Based on the EDX spectrum 143 obtained from the location C in the evaluated sample 129b, an average atomic number $Z_C$ of the evaluated sample 129b is calculated by the average atomic number calculation means 147 (step S103). The calculated average atomic number $Z_C$ of the evaluated sample can be displayed. Based on the calculated average atomic number $Z_C$ of the evaluated sample and the correlation database 149 between the average atomic numbers and the WDX background intensity values 51, a WDX background intensity value 51 for the evaluated sample is read out (step S104). Here, in the correlation database 149, the correlation data between the average atomic numbers and the WDX background data contains data obtained experimentally as a matter of course. Data not obtained experimentally is interpolated by experimental data or estimated based on the tendency of the experimental data. Consequently, the correlation database 149 is correlation database between all of the average atomic numbers and the WDX background intensity values 51.

Figure 16:
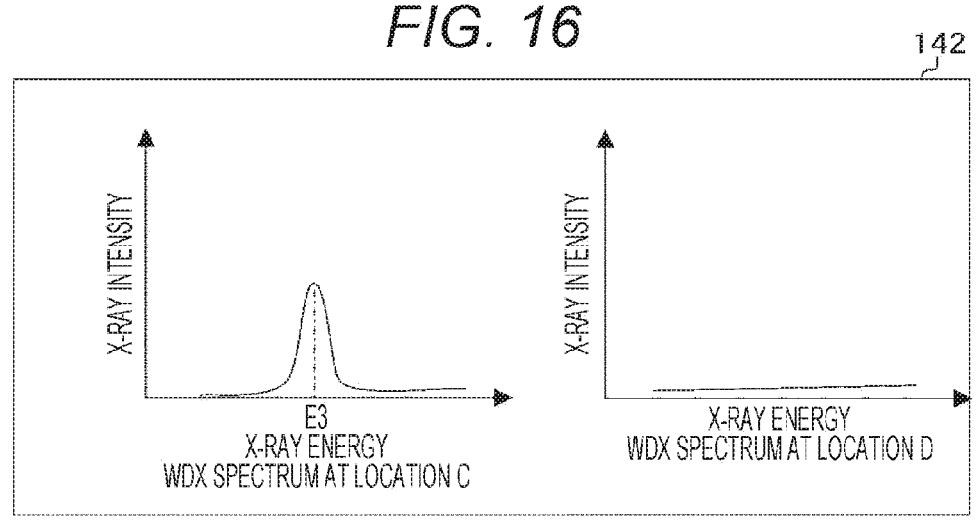
FIG. 16 is a display image illustrating examples of WDX spectra obtained in the electron beam analyzer according to Embodiment 1 or 2 of the present invention.
Figure 17:
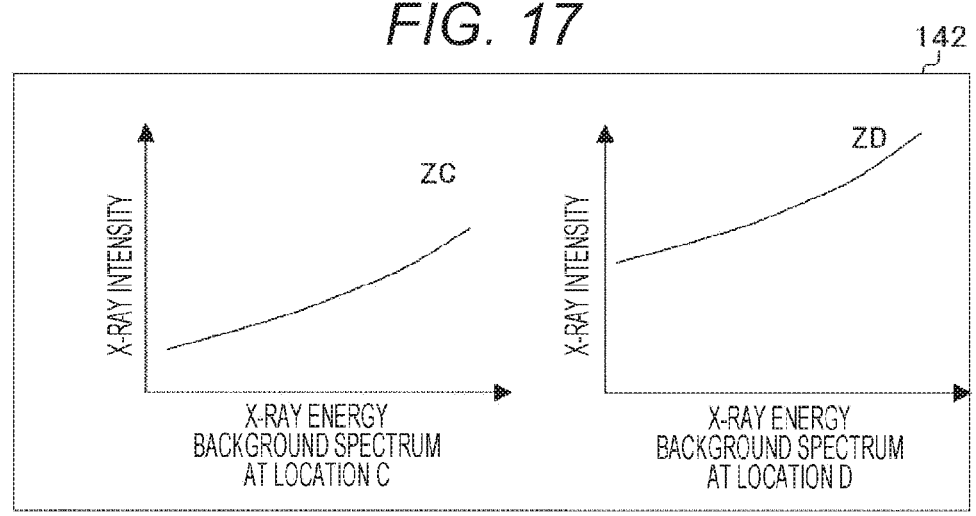
FIG. 17 is a display image illustrating examples of WDX backgrounds obtained in the electron beam analyzer according to Embodiment 1 or 2 of the present invention.

By means of the background elimination means, the WDX background intensity value 51 obtained in the step S104 is subtracted from the WDX spectrum obtained in the step S103 (step S105) to extract a peak of the light element (step S106). The same procedure as that for the location C is performed for the location D. The WDX spectra for the light element regions in the location C and the location D obtained in this manner are shown in FIG. 16. Both the WDX spectra for the location C and the location D are spectra from which the backgrounds as braking radiation have been eliminated. As for the location C, the clear light element X-ray peak can be obtained. As illustrated in FIG. 17, as the spectra 142, the backgrounds and the average atomic numbers Z for the location C and the location D calculated by the WDX background intensity calculation means can be displayed.

According to the present embodiment, the analysis electron microscope equipped with the X-ray analyzer having the braking radiation background processing means enables an X-ray analysis of a light element in a heavy metal with no braking radiation background variation along with an atomic number difference.

The EDX spectrometer 103b is used in the description of the background elimination means according to the present embodiment. However, since the atomic number is reflected in the backscattered electron, the backscattered electron detector 111 may be used.

Also, although only the atomic number is a background factor in the present embodiment, the amount and the energy of the primary electron beam 128 emitted to the sample 129 are also background factors. Thus, it is to be understood that the amount and the energy of the electron beam are included in the background processing means, and the amount and the energy of the electron beam can be monitored by the electron gun control unit 115.

When an analysis of boron in a permanent magnet was performed with use of the electron beam analyzer configured as in FIG. 1, an analysis sensitivity was improved. Also, when the analysis was performed with use of the flow illustrated in FIG. 13, a high-sensitivity analysis was performed efficiently. Further, in a case of using an ion beam instead of the electron beam, a high-sensitivity analysis was performed.

As described above, according to the present embodiment, it is possible to provide a charged particle beam analyzer and an analysis method enabling an efficient and high-sensitivity analysis of a microscopic light element contained in a heavy metal sample.

Embodiment 2

In the present embodiment, an example in which the electron beam analyzer 101 illustrated in FIG. 1 has been applied to map evaluation of a light element in a heavy metal will be described. A target sample for the map evaluation is the evaluated sample 129b used in Embodiment 1. It is to be noted that matters described in Embodiment 1 and not described in the present embodiment can be applied to the present embodiment unless the circumstances are exceptional.

An X-ray map image can be obtained by detecting an X-ray signal obtained in the WDX spectrometer 103a or the EDX spectrometer 103b in synchronization with a scanning signal of a primary electron beam as described in Embodiment 1. In EDX map evaluation, the EDX can detect the X-ray in a parallel manner, many element map images can be obtained simultaneously. As for a WDX map image, since the X-ray is detected in a serial manner by operating the diffraction grating and the detector, a map image is obtained per element.

The diffraction grating 113 and the WDX X-ray detector 114 are set and fixed so that the peak of the X-ray spectrum illustrated in FIG. 16 is the highest (energy position E3). Subsequently, each X-ray obtained in the WDX spectrometer 103a and the EDX spectrometer 103b is detected in synchronization with the primary electron beam 128. A WDX map image and an EDX map image are obtained simultaneously.

Figure 18:
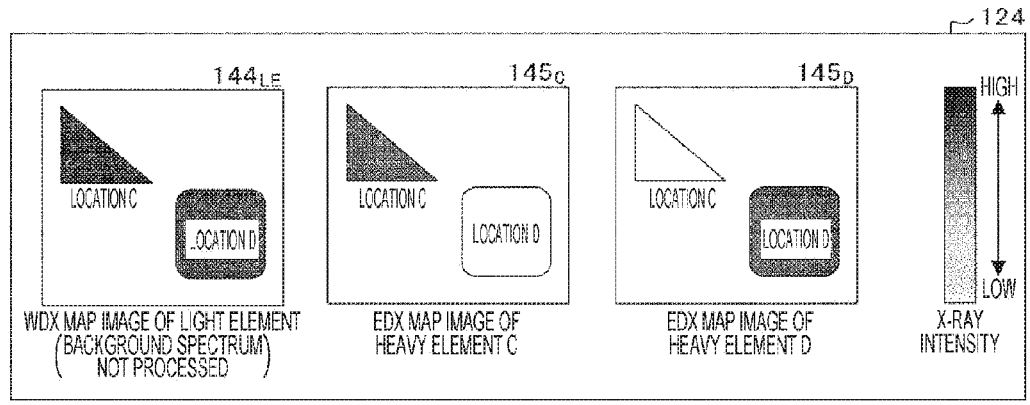
FIG. 18 is a display image illustrating examples of WDX map images obtained in the electron beam analyzer according to Embodiment 2 of the present invention.
Figure 19:
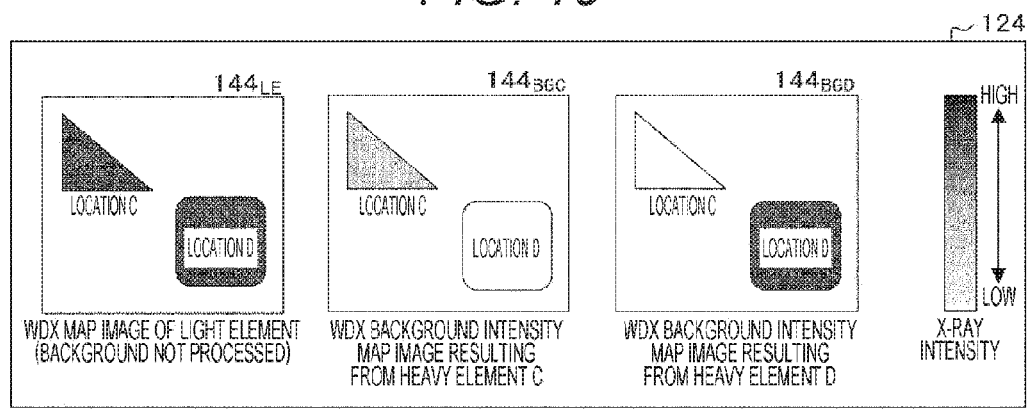
FIG. 19 is a display image illustrating examples of WDX map images obtained in the electron beam analyzer according to Embodiment 2 of the present invention.
Figure 20:
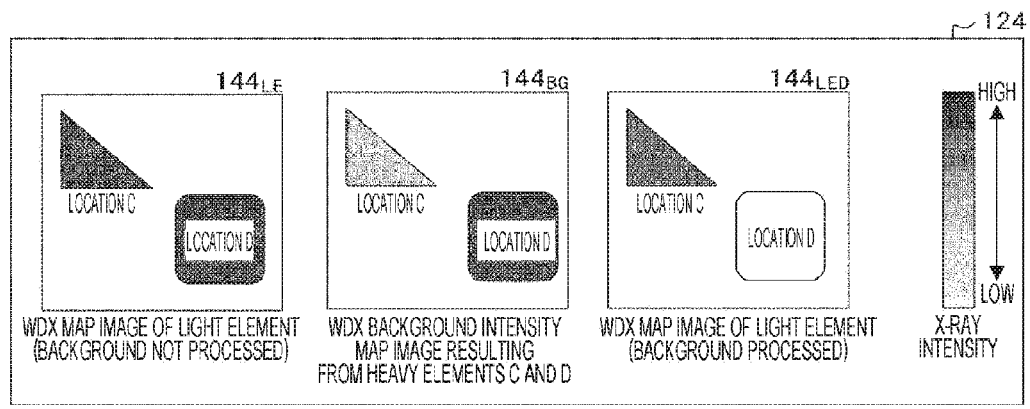
FIG. 20 is a display image illustrating examples of WDX map images obtained in the electron beam analyzer according to Embodiment 2 of the present invention.

In FIG. 18, a WDX map image $144_{LE}$ in which the background is not processed, an EDX map image $145_C$ for the heavy element C, and an EDX map image $145_D$ for the heavy element D are illustrated. Subsequently, by means of the background processing means 146, a WDX background intensity map $144_{BGC}$ resulting from the heavy element C is calculated from the obtained EDX map image $145_C$, and similarly, a WDX background intensity map $144_{BGD}$ resulting from the heavy element D is calculated from the EDX map image $145_D$. The respective WDX background map images can be displayed on the image display unit as illustrated in FIG. 19. The WDX background map images illustrated in FIG. 19 represent WDX background map images resulting from the heavy element C and the heavy element D, respectively. However, as in FIG. 20, a WDX background intensity map image $144_{BG}$ into which the WDX background intensity map image $144_{BGC}$ resulting from the heavy element C and the WDX background intensity map image $144_{BGD}$ resulting from the heavy element D overlap with each other can also be displayed. By subtracting the WDX background intensity map image $144_{BG}$ in FIG. 20 from the WDX map image $144_{LE}$ in which the background is not processed illustrated in FIG. 19 or 20, a WDX map image $144_{LED}$ of a light element in which only a light element peak is reflected can be obtained.

According to the present embodiment, the analysis electron microscope equipped with the X-ray analyzer having the braking radiation background processing means enables an X-ray map analysis of a light element with no braking radiation background variation in the map evaluation of the light element in a heavy metal.

Also, since obtainment of a background map image performed by the WDX, which is conventionally required for braking radiation background processing, can be dispensed with, map measurement time can be half as short as that in the conventional case.

Further, since changes of the background shape due to irradiation with the electron beam can be reduced much further than in a conventional case, a high-sensitivity analysis can be achieved.

Embodiment 3

In the present embodiment, in the electron beam analyzer 101 illustrated in FIG. 1, the background processing 146 including correction for absorption of a light element X-ray in consideration of absorption of the light element X-ray by the sample 129 itself will be described. It is to be noted that matters described in Embodiment 1 or 2 and not described in the present embodiment can be applied to the present embodiment unless the circumstances are exceptional.

As described in the Technical Problem section, a light element X-ray, which is low in energy, is easy to be absorbed into a substance, and X-ray absorption into a heavy element is especially significant (The absorption amount largely depends on the atomic number or the like of the heavy element). Since absorption of the light element X-ray changes depending on the difference of the average atomic number of the heavy element, a high-sensitivity analysis of the light element X-ray contained in the heavy element sample is difficult. In the present embodiment, with use of a means for correcting changes in detection intensity of the light element X-ray caused by in-sample variation of the average atomic number or the like of the heavy element, a high-sensitivity analysis is achieved.

In the present embodiment, the background processing means 146 includes a means for obtaining a background data 51d containing a light element X-ray spectrum with use of a standard sample 129d containing a light element, a peak intensity measurement means, and a means for correcting absorption of a light element X-ray into a heavy element based on the background data 51d containing the light element X-ray spectrum.

Figure 21:
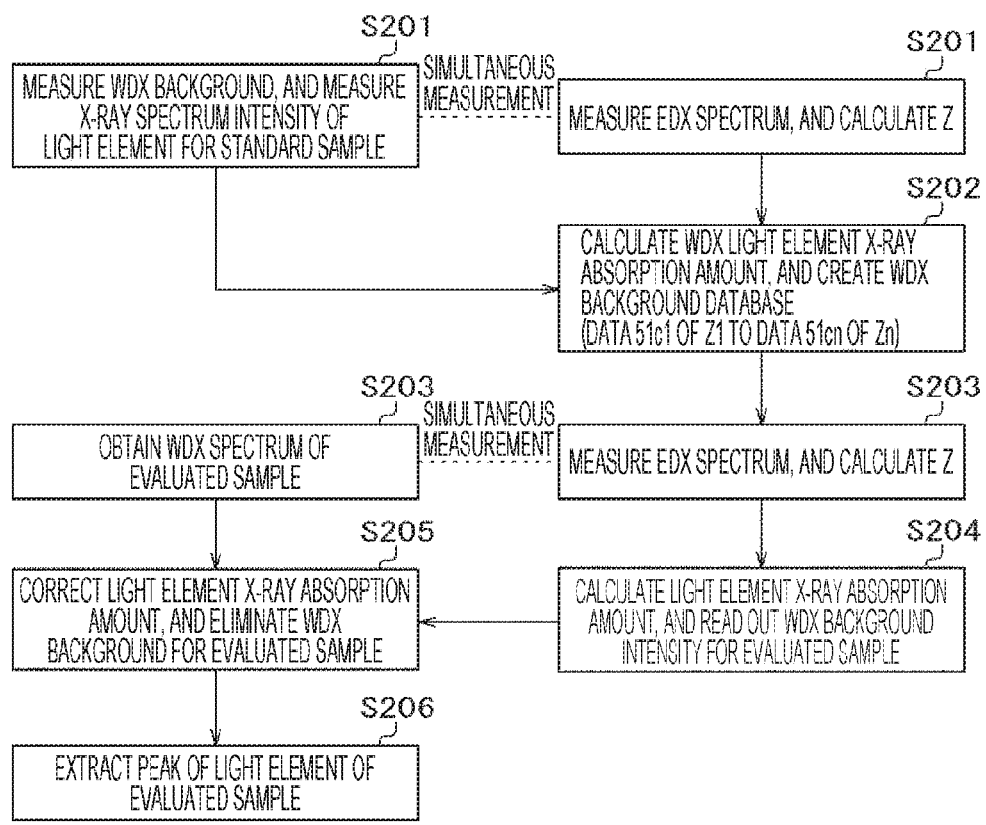
FIG. 21 is a flowchart illustrating an example of background and absorption correction processing in an analysis method according to Embodiment 3 of the present invention.
Figure 22:
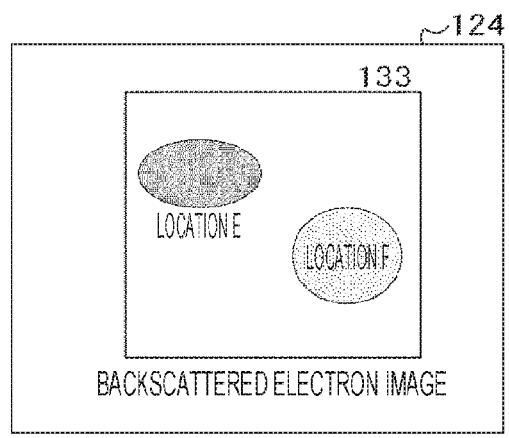
FIG. 22 is a schematic plan view illustrating an example of a sample used for evaluation in Embodiment 3 of the present invention.

FIG. 21 is an example of a flow illustrating the present method. A backscattered electron image of an evaluated sample 129c is illustrated in FIG. 22. Heavy element (a heavy element E and a heavy element F) regions in a location E and a location F are evaluated. The average atomic numbers of the location E and the location F are $Z_E$ and $Z_F$. The atomic number $Z_F$ is higher than the atomic number $Z_E$.

In a similar manner to that in Embodiment 1, a WDX spectrum 142d1 and an EDX spectrum 143d1 for a standard sample 129d1 containing a light element having a known concentration are simultaneously obtained by the WDX spectrometer 103a and the EDX spectrometer 103b. The energy range of the WDX spectrum 142d is a low energy region for detecting a light element. Based on the obtained EDX spectrum 143d1, an average atomic number Za1 is calculated by the average atomic number calculation means 147, and based on the WDX spectrum 142d1, X-ray spectrum intensity of the light element having the known concentration is measured (step S201).

Figure 23:
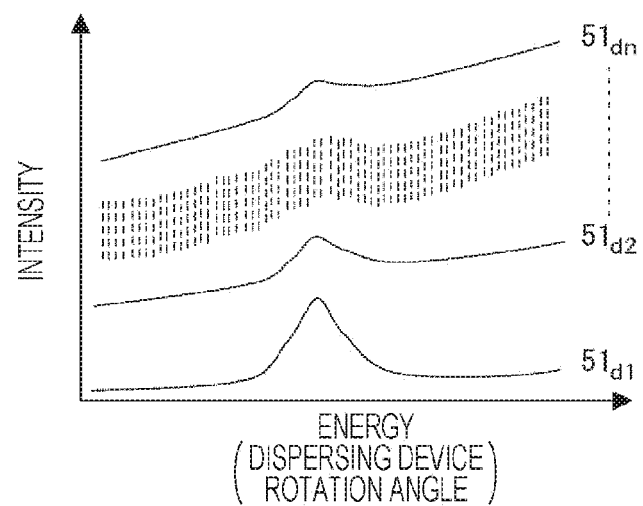
FIG. 23 illustrates WDX spectrum data each containing a light element X-ray peak per average atomic obtained in an electron beam analyzer according to Embodiment 3 of the present invention.
Figure 24:
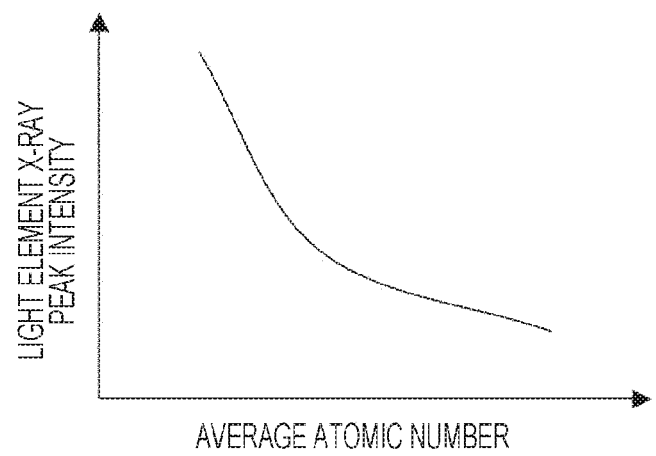
FIG. 24 illustrates relationship between the average atomic number and light element X-ray peak intensity obtained in the electron beam analyzer according to Embodiment 3 of the present invention.
Figure 25:
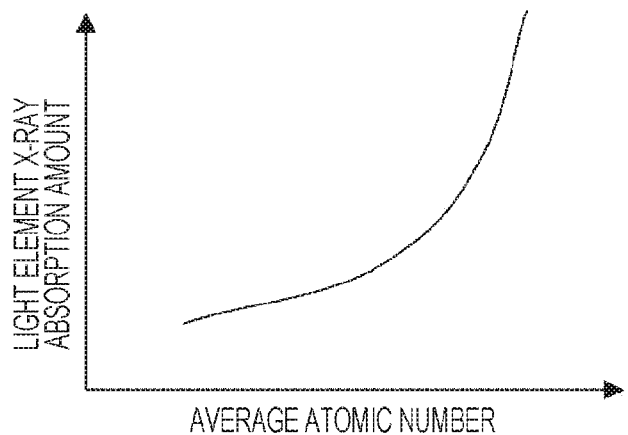
FIG. 25 illustrates relationship between the average atomic number and the light element X-ray absorption amount obtained in the electron beam analyzer according to Embodiment 3 of the present invention.

The measured WDX spectrum 142d1 is the background data 51a1 containing the light element X-ray peak and becomes a background data 51d1 containing the light element X-ray peak having the average atomic number Za1 as illustrated in FIG. 23. The series of operations in the step S201 are performed with use of a plurality of standard samples 129d1 to 129dn to obtain background data 51d1 to background data 51dn of WDX spectra each containing the light element X-ray peak having average atomic numbers Z1 to Zn illustrated in FIG. 23 (step S202). Also, based on average atomic number dependency data on light element X-ray intensity illustrated in FIG. 24 obtained from the background data each containing the light element X-ray peak, average atomic number dependency data on the light element X-ray absorption amount (FIG. 25) is calculated.

Subsequently, a WDX spectrum 142 and an EDX spectrum 143 for the location E in an evaluated sample 129c containing a light element sample in a heavy element are obtained by the WDX spectrometer 103a and the EDX spectrometer 103b, respectively. Based on the EDX spectrum 143 obtained from the location E in the evaluated sample 129c, an average atomic number $Z_E$ of the evaluated sample 129c is calculated by the average atomic number calculation means 147 (step S203). Based on the calculated average atomic number $Z_E$ of the evaluated sample and a correlation database 149 (FIG. 23) between the average atomic numbers and the WDX background intensity values 51d each containing the light element X-ray peak, a WDX background intensity value 51 for the light element X-ray evaluated sample is read out (step S204). Also, based on the average atomic number $Z_E$ calculated by the average atomic number calculation means 147 and the average atomic number dependency data on the light element X-ray absorption amount illustrated in FIG. 25, the light element X-ray absorption amount at the average atomic number $Z_E$ is calculated. The X-ray absorption rate or the X-ray absorption amount per light element in relation to the average atomic number can be displayed on any of the display units included in the charged particle beam analyzer.

By means of the background elimination means, the WDX background intensity value 51 obtained in the step S204 is subtracted from the WDX spectrum obtained in the step S203. Also, by means of the light element X-ray absorption correction means, the absorption amount at the average atomic number $Z_E$ in the WDX spectrum peak obtained in the step S203 is corrected (step S205), and a peak of the light element is extracted (step S206).

Figure 26:
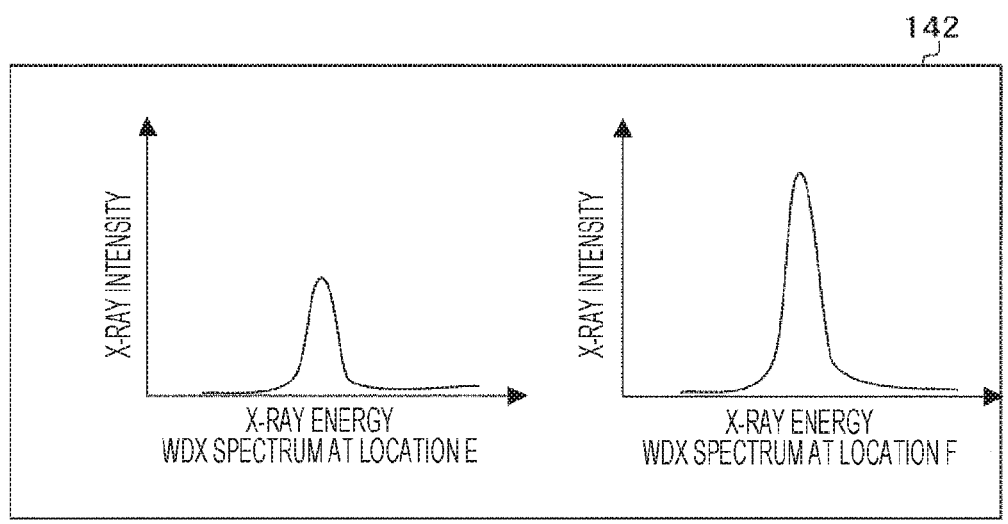
FIG. 26 illustrates WDX spectra obtained in the electron beam analyzer according to Embodiment 3 of the present invention.

The same light element X-ray analysis as that for the location E is performed for the location F. The WDX spectra for the light element regions in the location E and the location F obtained in this manner are shown in FIG. 26.

Figure 27:
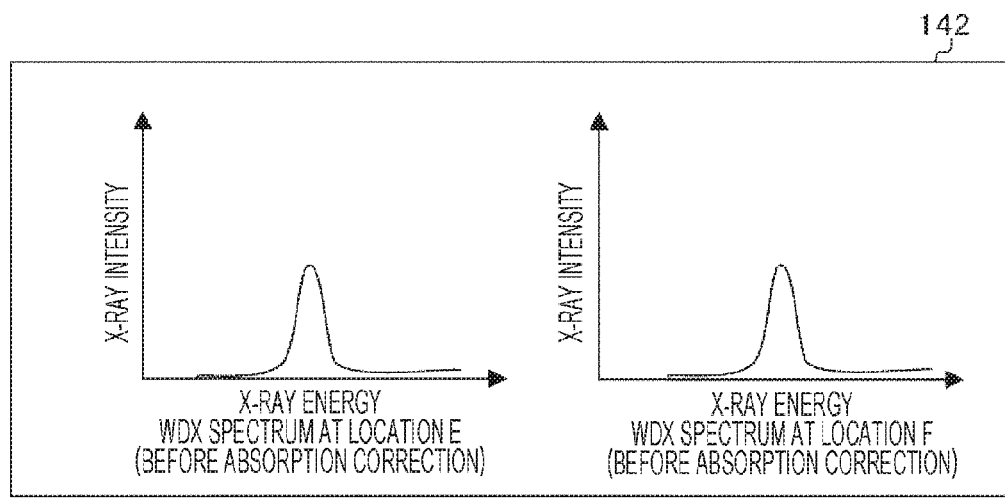
FIG. 27 illustrates WDX spectra before absorption correction obtained in the electron beam analyzer according to Embodiment 3 of the present invention.

Also, FIG. 27 illustrates data after the background elimination and before the light element X-ray absorption correction. As is apparent from FIG. 26, both the WDX spectra for the location E and the location F are spectra from which the backgrounds as braking radiation have been eliminated. Also, in FIG. 27, which illustrates the results before the absorption correction, the light element X-ray peak intensity values are equivalent. However, by using the light element X-ray absorption correction means according to the present embodiment, in FIG. 26, the light element X-ray peak intensity in the location F is higher than that in the location E, and it is found that the location F has a high light element concentration. In the location F, the high atomic number $Z_F$ absorbs much light element X-ray, and the amount of the light element X-ray to be absorbed is larger in the location F than that in the location E (FIG. 26). In the present embodiment, the light element X-ray absorption amount difference along with the atomic number difference can be corrected (FIG. 27).

According to the present embodiment, by using the analysis electron microscope equipped with the X-ray analyzer having the absorption correction means for correcting absorption of light element X-ray into a sample in an analysis of a light element in a heavy metal, absorption of the light element X-ray into the sample itself is corrected, and a high-sensitivity light element spectrum analysis is thus enabled. Similarly, in terms of the light element map evaluation, by applying the present embodiment to Embodiment 2, a high-sensitivity light element map image can be obtained.

Figure 28:
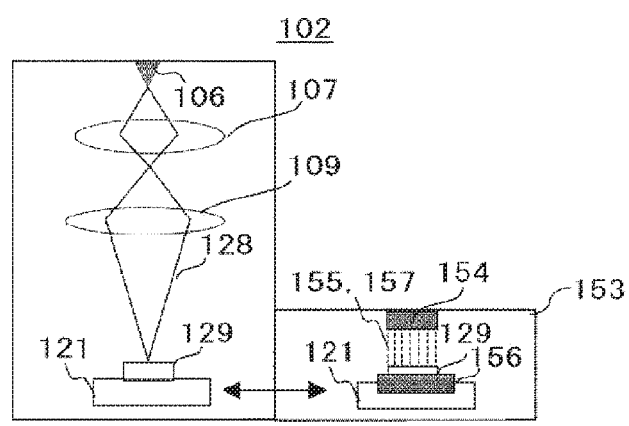
FIG. 28 is a schematic cross-sectional view illustrating a surface processing means in the electron beam analyzer according to Embodiment 3 of the present invention.

In the present embodiment, when the WDX light element absorption amount and the WDX background database are to be obtained in the step S202, the sample surface is got in a clean state before obtaining the WDX background data containing the light element peak to enable a more accurate light element analysis. To clean the surface of the standard sample 129 before measurement of the WDX spectrum, the scanning electron microscope device 102 of the electron beam analyzer 101 is provided in a sample exchange chamber 153 with a sample surface cleaning means 154 or 156 for cleaning the sample surface as illustrated in FIG. 28 although it is not particularly described in the present embodiment. The sample surface cleaning means 154 may be an ion irradiation device irradiating the sample surface with ions 155 in plasma 157, or the sample surface cleaning means 156 may be a sample heating means for heating the sample with use of exhaust air in the sample exchange chamber 153 to evaporate substances on the sample surface.

When an analysis of boron in a permanent magnet was performed with use of the electron beam analyzer illustrated in FIG. 1 further including the light element X-ray absorption correction means, an analysis sensitivity was further improved. Also, when the analysis was performed with use of the flow illustrated in FIG. 13, a higher-sensitivity analysis was performed efficiently. Further, in a case of using an ion beam instead of the electron beam, a high-sensitivity analysis was performed.

As described above, according to the present embodiment, it is possible to provide a charged particle beam analyzer and an analysis method enabling an efficient and higher-sensitivity analysis of a microscopic light element contained in a heavy metal sample.

Although the invention achieved by the present inventors has been described specifically based on the embodiments, it is to be understood that the present invention is not limited to the foregoing embodiments and can be altered in various ways without departing from the scope of the present invention. For example, the foregoing embodiments have been described in detail to facilitate understanding of the present invention, and the present invention is not limited to one including all of the components described herein. Also, some components of one embodiment can be substituted with components of another embodiment, and components of another embodiment can be added to components of one embodiment. Further, some components of each embodiment can be added, deleted, and substituted with other components.

REFERENCE SIGNS LIST 101 electron beam analyzer
102 scanning electron microscope device
103 X-ray analysis device
103a WDX spectrometer
103b EDX spectrometer
104 control system
105 operation unit
106 electron gun
107 condenser lens
108 electron beam deflector
109 objective lens
110 secondary electron detector
111 backscattered electron detector
112 X-ray condensing lens
113 diffraction grating
113a flat-shaped diffraction grating
113b curved diffraction grating
114 WDX X-ray detector
115 electron gun control unit
116 condenser lens control unit
117 electron beam deflector control unit
118 objective lens control unit
119 secondary electron detection system circuit control unit
120 backscattered electron detection system circuit control unit
121 sample stage
122 WDX X-ray detection system circuit control unit
123 EDX X-ray detection system circuit control unit
124 image display unit
125 X-ray spectrum display unit
126 storage unit
127 operating screen
128 primary electron beam
129 sample
129a, 129d standard sample
129b evaluated sample
129c evaluated sample containing a light element
130 secondary electron
131 backscattered electron
132 secondary electron image
133 backscattered electron image
134 X-ray
135 X-ray lens driving unit
136 X-ray condensing lens driving control unit
137 diffraction grating driving unit
138 diffraction grating driving control unit
139 WDX detector driving unit
140 stage control unit
141 WDX X-ray detector driving control unit
142 WDX spectrum
142a1 WDX spectrum for a standard sample 29a1
143 EDX spectrum
143a1 EDX spectrum for a standard sample 29a1
144 WDX map image
145 EDX map image
146 WDX background processing means
147 average atomic number calculation means
148 WDX background measurement means
149 correlation data between average atomic numbers and WDX background intensity values
150 correlation data calculation means
51 WDX background intensity value
51a1 to 51an WDX background data for standard samples 129a1 to 129an
51d1 to 51dn WDX background data each containing a light element X-ray peak for standard samples 129d1 to 129dn
153 sample exchange chamber
154, 156 sample surface cleaning means
155 ion
157 plasma

The invention claimed is:

1. A charged particle beam analyzer comprising a charged particle beam optical system, a sample stage for mounting a sample thereon, an X-ray spectrometer, a control unit, and an operation unit, and controlling the charged particle beam optical system by means of the control unit to irradiate the sample with a charged particle beam, detecting an X-ray generated from the sample by means of the X-ray spectrometer, and analyzing the sample with use of detected information by means of the operation unit, wherein
the X-ray spectrometer is a wavelength dispersive X-ray spectrometer (WDX spectrometer), and
the operation unit includes:
a storage unit having stored therein a correlation database between a plurality of average atomic numbers and WDX background intensity values obtained with use of a plurality of standard samples; and
a WDX background processing means including an average atomic number calculation means for calculating an average atomic number for the sample and a background elimination means for eliminating a WDX background intensity value derived from the average atomic number for the sample calculated by the average atomic number calculation means and the correlation database stored in the storage unit from a WDX spectrum for the sample obtained with use of the X-ray spectrometer.

2. The charged particle beam analyzer according to claim 1, wherein the average atomic number calculation means uses information detected in an energy dispersive X-ray spectrometer (EDX spectrometer).

3. The charged particle beam analyzer according to claim 1, wherein the average atomic number calculation means uses information detected in a backscattered electron detector.

4. The charged particle beam analyzer according to claim 2, wherein the average atomic number calculated by the average atomic number calculation means is displayed on any of display units included in the charged particle beam analyzer.

5. The charged particle beam analyzer according to claim 1, wherein
each of the plurality of standard samples contains a light element having a known concentration, and
the storage unit has stored therein correlation data between the average atomic numbers and WDX light element X-ray peak intensity values for correcting a light element X-ray amount to be absorbed in the sample.

6. The charged particle beam analyzer according to claim 5, wherein an X-ray absorption rate or an X-ray absorption amount of the light element in relation to the average atomic number obtained from the average atomic number and the WDX X-ray peak detected are displayed on any of the display units included in the charged particle beam analyzer.

7. The charged particle beam analyzer according to claim 1, further comprising a sample surface cleaning means for cleaning a surface of the sample.

8. The charged particle beam analyzer according to claim 7, wherein the sample surface cleaning means includes an ion or plasma irradiation mechanism.

9. The charged particle beam analyzer according to claim 7, wherein the sample surface cleaning means includes a sample heating mechanism.

10. A charged particle beam analyzer comprising a charged particle beam optical system, a sample stage for mounting a sample thereon, an X-ray spectrometer, a control unit, and an operation unit, and controlling the charged particle beam optical system by means of the control unit to irradiate the sample with a charged particle beam, detecting an X-ray generated from the sample by means of the X-ray spectrometer, and performing map evaluation for the sample with use of detected information, wherein
the X-ray spectrometer is a wavelength dispersive X-ray spectrometer (WDX spectrometer), and
the operation unit includes:
a storage unit having stored therein a correlation database between a plurality of average atomic numbers and WDX background intensity values obtained with use of a plurality of standard samples;
a WDX background processing means including an average atomic number calculation means for calculating an average atomic number map with use of X-ray energy corresponding to a specific light element on a surface of the sample and a background elimination means for eliminating a WDX background intensity map derived from the average atomic number map for the surface of the sample calculated by the average atomic number calculation means and the correlation database stored in the storage unit from a WDX spectrum map for the sample obtained with use of the X-ray spectrometer; and
an image display unit for displaying the WDX background intensity map derived from the correlation database stored in the storage unit.

11. The charged particle beam analyzer according to claim 10, wherein the image display unit displays a map image into which the WDX background intensity map derived from the average atomic number map for the surface of the sample calculated by the average atomic number calculation means and the correlation database stored in the storage unit is eliminated from the WDX spectrum map for the sample obtained with use of the X-ray spectrometer.

12. An analysis method comprising:
a first step of creating a correlation database between a plurality of average atomic numbers and WDX background intensity values with use of a plurality of standard samples and storing the correlation database in a storage unit; and
a second step of calculating an average atomic number for an evaluated sample and eliminating a WDX background intensity value derived from the calculated average atomic number for the evaluated sample and the correlation database stored in the storage unit from a WDX spectrum for the sample obtained with use of a wavelength dispersive X-ray spectrometer.

13. The analysis method according to claim 12, wherein the average atomic number is obtained with use of an energy dispersive X-ray spectrometer.

14. The analysis method according to claim 12, wherein the average atomic number is obtained with use of a backscattered electron detector.

15. The analysis method according to claim 12, wherein each of the plurality of standard samples contains a light element having a known concentration, and
the storage unit has stored therein correlation data between the average atomic numbers and WDX light element X-ray peak intensity values for correcting a light element X-ray amount to be absorbed in the sample.

* * * * *